United States Patent [19]

Yamaguchi

[11] Patent Number: 4,712,564
[45] Date of Patent: Dec. 15, 1987

[54] BLOOD PRESSURE MEASURING APPARATUS

[75] Inventor: Keiji Yamaguchi, Shimizu, Japan
[73] Assignee: Terumo Corporation, Tokyo, Japan
[21] Appl. No.: 828,189
[22] Filed: Feb. 11, 1986
[30] Foreign Application Priority Data Feb. 13, 1985 [JP] Japan .................................. 60-24460

[51] Int. Cl.⁴ .............................................. A61B 5/02
[52] U.S. Cl. .................................... 128/682; 128/683
[58] Field of Search ................ 128/672, 677, 680-683, 128/686

[56] References Cited

U.S. PATENT DOCUMENTS 4,273,136  6/1981  Kubo et al. ......................... 128/680
4,338,949  7/1982  Croslin .............................. 128/677
4,501,281  2/1985  Furukawa ........................ 128/677 X
4,549,549 10/1985  Furukawa ........................ 128/677 X

OTHER PUBLICATIONS

Chungcharoen, "Genesis of Korotkoff Sounds", *Amer. J. Phys.*, vol. 207, No. 1, 7-1964, pp. 190-194.

Primary Examiner—Kyle L. Howell
Assistant Examiner—Angela D. Sykes
Attorney, Agent, or Firm—Staas & Halsey

[57] ABSTRACT

A blood pressure measuring apparatus displays that pressurization of a pressure cuff affixed to a patient is inadquate when elapsed time from the start of cuff depressurization to the detection of an initial sound of blood flow through the patient's blood vessel is shorter than a time interval between adjacent blood flow sounds, which interval approximately coincides with the patient's pulse interval.

16 Claims, 13 Drawing Figures

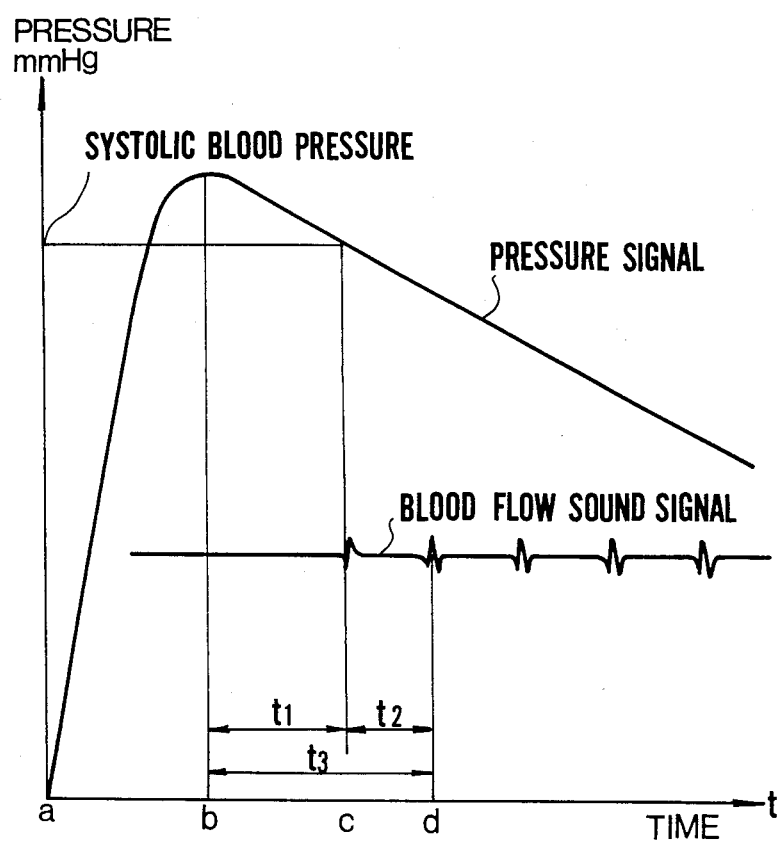

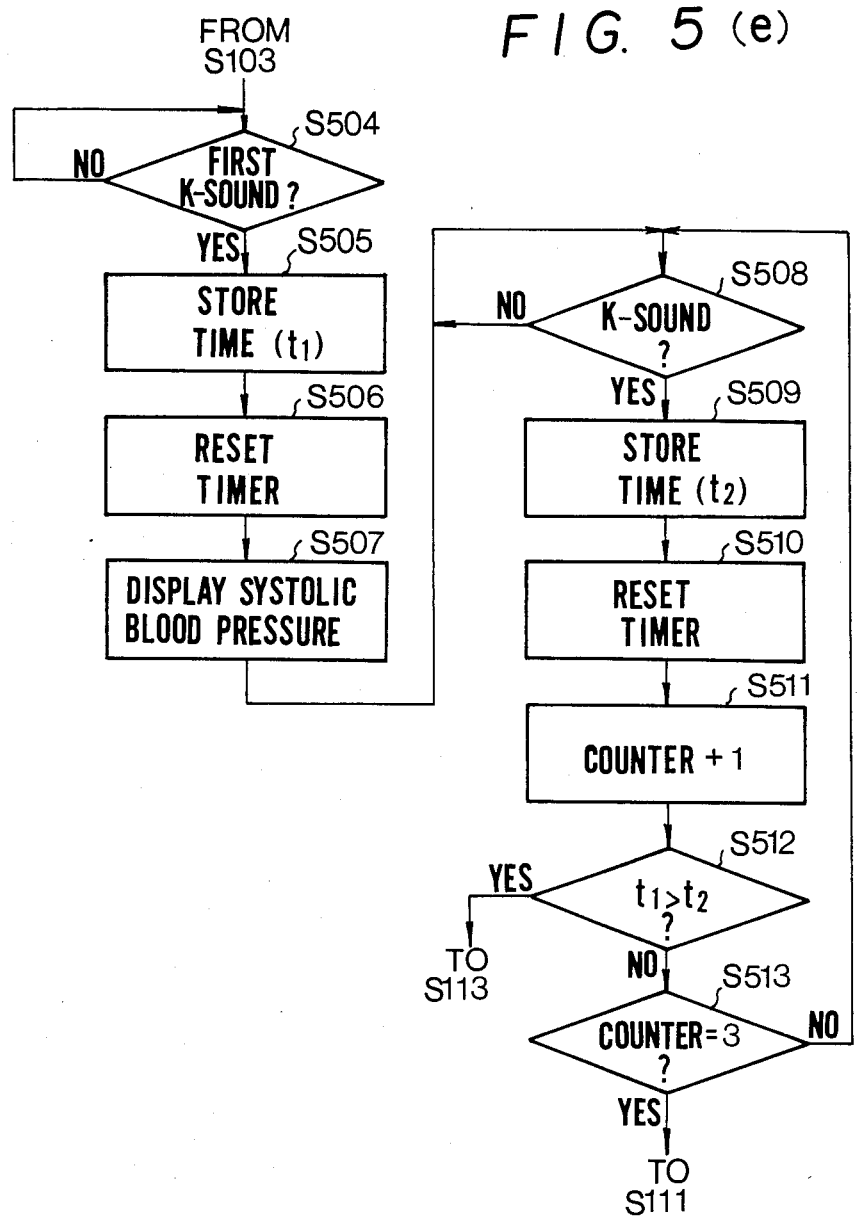

BLOOD PRESSURE MEASURING APPARATUS

BACKGROUND OF THE INVENTION

1. Field of the Invention

This invention relates a blood pressure measuring apparatus capable of automatically sensing inadequate pressurization.

2. Description of the Related Art

In a blood pressure measuring apparatus which operates on the basis of the Korotkoff method, determining inadequacy of pressurization in the prior art is based on whether Korotkoff sounds are detected within a prescribed period of time following the start of blood pressure measurement, i.e., following termination of the pressurizing operation. For example, see the specification of Japanese Utility Model Publication No. 57-3296.

A problem with the foregoing method of determination is that there is no assurance that the prescribed period of time is long enough to allow fail-safe detection of inadequate pressurization under all conditions. For this reason, there is always the possibility that inadequate pressurization will not be sensed in case of a low pulse rate. If it is attempted to solve this problem by making the set period of time long enough to sense inadequate pressurization without fail even for low pulse rates, then a patient with a comparatively rapid pulse must be subjected to more pressurization than necessary and will experience discomfort due to the pressure applied. Another problem involved with rapid pulses is that inadequate pressurization is sometimes sensed even if enough pressure is actually applied. As a result, the patient is subjected to unnecessary repressurization.

SUMMARY OF THE INVENTION

The present invention has been devised to solve the aforementioned problems encountered in the prior art.

Accordingly, an object of the present invention is to provide a blood pressure measuring apparatus which makes it possible to sense whether or not pressurization is inadequate in a reliable manner without subjecting a patient with a rapid pulse to more pressure than necessary, and which will not mistakenly judge that pressurization is inadequate when such is not actually the case.

Another object of the present invention is to provide a blood pressure measuring apparatus which will sense inadequate pressurization without fail even when applied to a patient with a low pulse rate.

Still another object of the present invention is to provide a blood pressure measuring apparatus capable of judging inadequate pressurization without being influenced by differences in pulse from one individual to another.

A further object of the present invention is to provide a blood pressure measuring apparatus free of measurement errors attributable to differences among individuals.

According to the present invention, the foregoing objects are attained by providing a blood pressure measuring apparatus comprising pressurizing means for feeding a fluid into a pressure cuff to effect pressurization thereof, sensing means for sensing a blood flow sound produced by a blood vessel when the pressurized pressure cuff is depressurized and for producing an output signal indicative of the blood flow sound, and decision means for deciding whether pressurization is inadequate in accordance with the output signal from the sensing means and on the basis of a relationship between elapsed time from the start of depressurization to the occurrence of the initial blood flow sound and the time interval between blood flow sounds.

In a preferred embodiment of the invention, the fluid fed into the pressure cuff is air.

In a preferred embodiment of the invention, the sensing means discriminates a Korotkoff sound from the blood flow sound produced by the blood vessel.

In a preferred embodiment of the invention, the decision means decides that pressurization is inadequate if the elapsed time from the start of depressurization to the occurrence of the initial blood flow sound is shorter than the time interval between blood flow sounds.

In another aspect of the invention, the blood pressure measuring apparatus comprises pressurizing means for feeding a fluid into a pressure cuff to effect pressurization thereof, sensing means for sensing a blood flow sound produced by a blood vessel when the pressurized pressure cuff is depressurized, first measuring means for measuring elapsed time from the start of depressurization to the occurrence of the initial blood flow sound, second measuring means for measuring elapsed time from the start of pressurization to the occurrence of a second blood flow sound, and decision means for deciding whether pressurization is inadequate based on results obtained by comparing the elapsed time measured by the first measuring means and the elapsed time measured by the second measuring means.

In a preferred embodiment of the invention, the fluid fed into the pressure cuff is air.

In a preferred embodiment of the invention, the sensing means discriminates a Korotkoff sound from the blood flow sound produced by the blood vessel.

In a preferred embodiment of the invention, the decision means decides that pressurization is inadequate if the elapsed time from the start of depressurization to the occurrence of the initial blood flow sound is shorter than the time interval between blood flow sounds.

In another aspect of the invention, the blood pressure measuring apparatus comprises pressurizing means for feeding a fluid into a pressure cuff to effect pressurization thereof, sensing means for sensing a blood flow sound produced by a blood vessel when the pressurized pressure cuff is depressurized, first measuring means for measuring elapsed time from the start of depressurization to the occurrence of the initial blood flow sound, second measuring means for measuring elapsed time from the occurrence of the initial blood flow sound to the occurrence of a second blood flow sound, and decision means for deciding whether pressurization is inadequate based on results obtained by comparing the elapsed time measured by the first measuring means and the elapsed time measured by the second measuring means.

In a preferred embodiment of the invention, the fluid fed into the pressure cuff is air.

In a preferred embodiment of the invention, the sensing means discriminates a Korotkoff sound from the blood flow sound produced by the blood vessel.

In a preferred embodiment of the invention, the decision means decides that pressurization is inadequate if the elapsed time from the start of depressurization to the occurrence of the initial blood flow sound is shorter than the time interval between blood flow sounds.

In another aspect of the invention, the blood pressure measuring apparatus comprises pressurizing means for feeding a fluid into a pressure cuff to effect pressurization thereof, sensing means for sensing a blood flow sound produced by a blood vessel when the pressurized pressure cuff is depressurized, first measuring means for measuring elapsed time from the start of depressurization to the occurrence of the initial blood flow sound, second measuring means for measuring, after a predetermined period of time, elapsed time within which at least two blood flow sounds are sensed, and decision means for deciding whether pressurization is inadequate based on results obtained by comparing the elapsed time measured by the first measuring means and the elapsed time measured by the second measuring means.

In a preferred embodiment of the invention, the fluid fed into the pressure cuff is air.

In a preferred embodiment of the invention, the sensing means discriminates a Korotkoff sound from the blood flow sound produced by the blood vessel.

In a preferred embodiment of the invention, the decision means decides that pressurization is inadequate if the elapsed time from the start of depressurization to the occurrence of the initial blood flow sound is shorter than the time interval between blood flow sounds.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 3 is a timing chart illustrating a process for detecting systolic blood pressure;

DETAILED DESCRIPTION

An embodiment of the present invention will now be described in detail with reference to the accompanying drawings.

Figure 1:
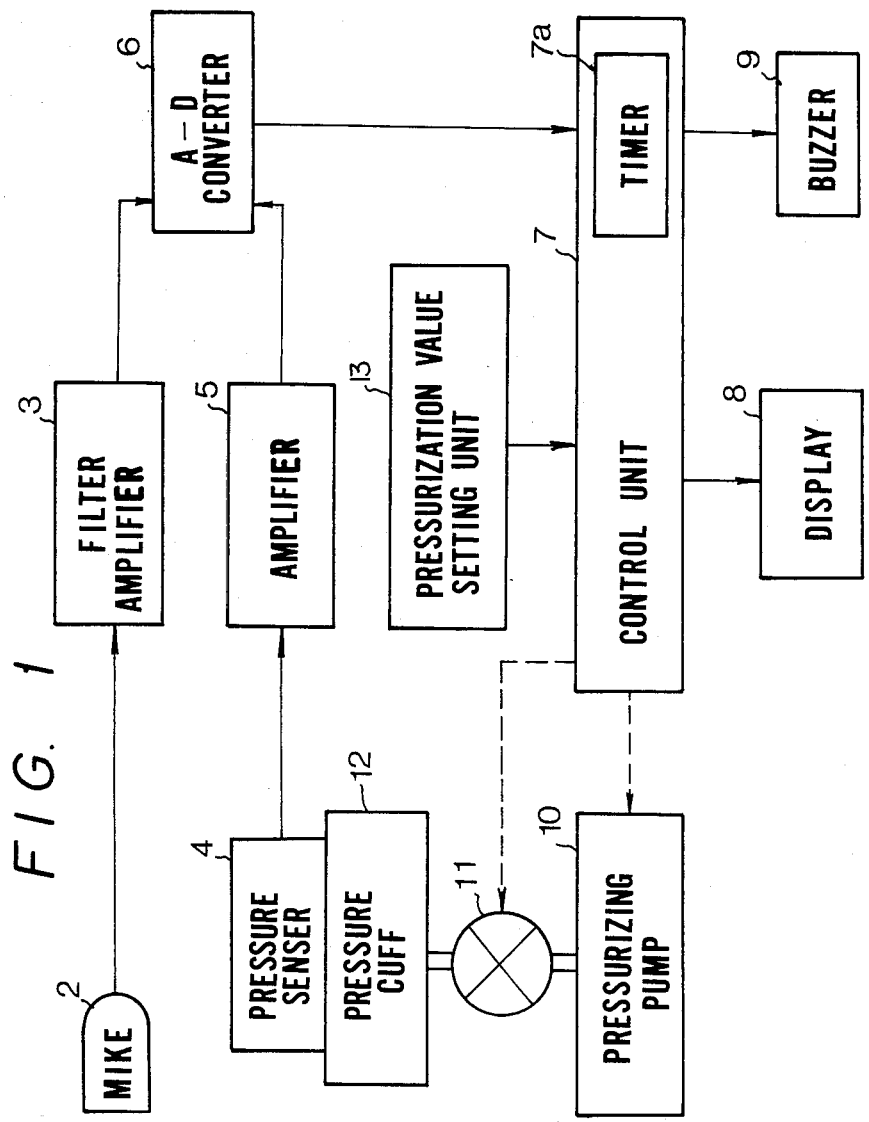
FIG. 1 is a block diagram illustrating an embodiment of a blood measuring apparatus according to the present invention.

FIG. 1 illustrates an embodiment of a blood pressure measuring apparatus according to the present invention. The apparatus includes a microphone 2 attached to the lower edge of a pressure cuff 12 so that the microphone will be positioned near the bend in a patient's forearm opposite the elbow when the the cuff 12 is affixed to the upper portion of the patient's arm. The microphone 2 is adapted to detect the sound of blood flow through a blood vessel and to produce an output signal indicative thereof. This output signal is applied to a filter amplifier 3 for selecting and amplifying a required frequency component of the signal. Also attached to the pressure cuff 12 is a pressure sensor 4 for sensing pressure and for producing an output signal indicative of the pressure sensed. This signal is amplified by an amplifier 5. The outputs of the filter amplifier 3 and amplifier 5, both of which are analog signals, are applied to an A-D converter 6 which converts these signals into digital signals. The digital output of the A-D converter 6 is inputted to a control unit 7. The latter, which is preferably of one-chip microprocessor construction, detects a Korotkoff sound from the signal indicative of the blood flow sound produced by microphone 2, detects the pressure of cuff 12 that prevails when the Korotkoff sound is detected, executes blood pressure measurement processing on the basis of the detected Korotkoff sound and detected pressure, and causes a display 8 to display the results of such processing, such as systolic and diastolic blood pressure. The control unit 7 is connected to a buzzer 9. A pressurizing pump 10 is connected to the pressure cuff 12 through a discharge valve 11. Also connected to the control unit 7 is a setting unit 13 for setting the pump 10 to a pressurization value through the intermediary of the control unit. Numeral 7a denotes a timer circuit incorporated within the control unit 7.

Figure 2:
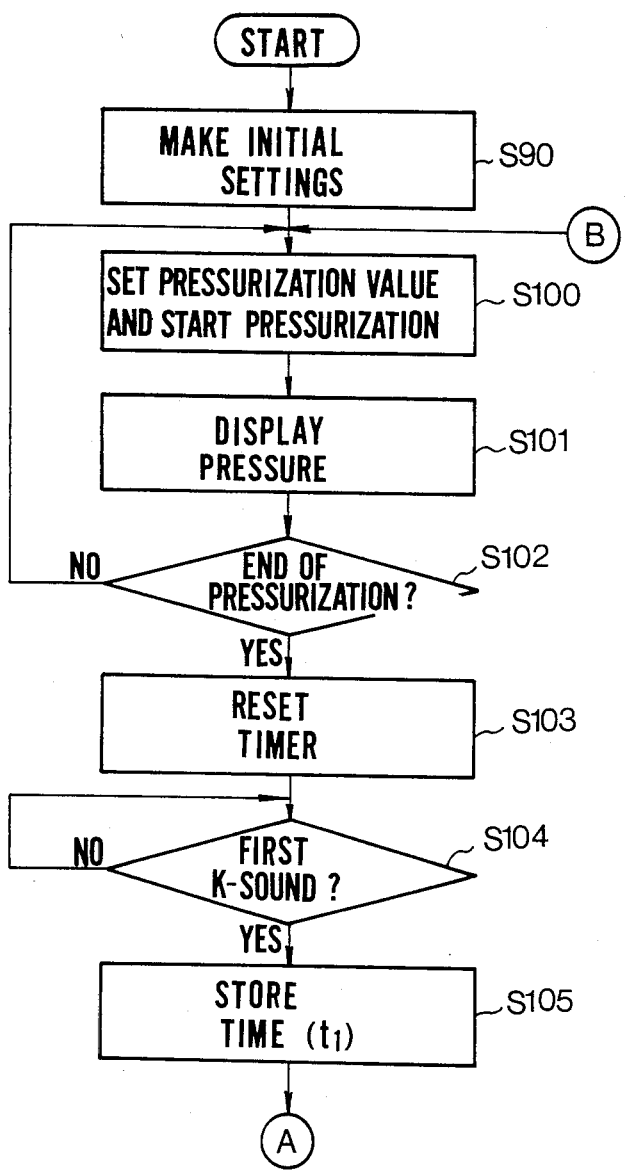
FIGS. 2(a) and 2(b) form a flowchart illustrating control of blood pressure measurement in the apparatus of FIG. 1.
Figure 2B:
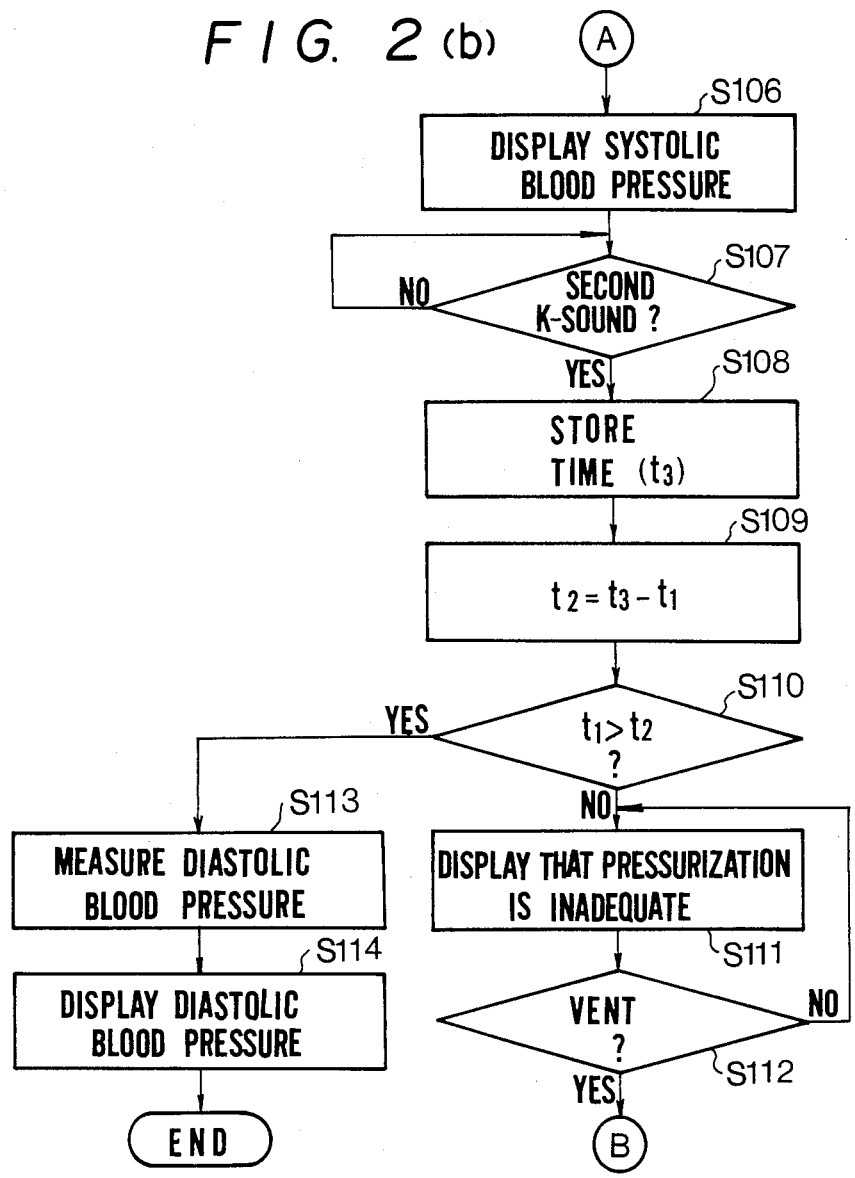
Figure 4A:
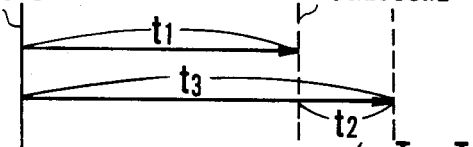
FIGS. 4(a)–4(e) are timing diagrams useful in describing control of blood pressure measuring according to other embodiments of the present invention.
Figure 4B:
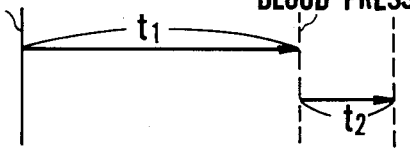
Figure 4C:
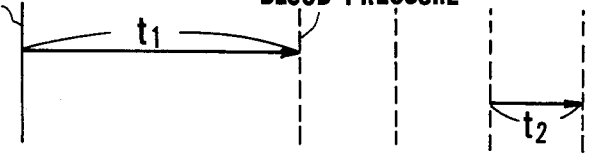
Figure 4D:
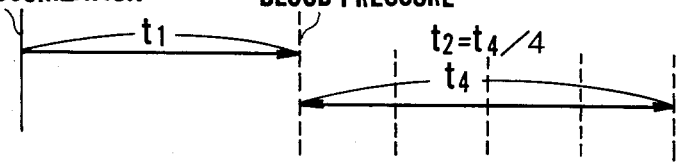
Figure 4E:
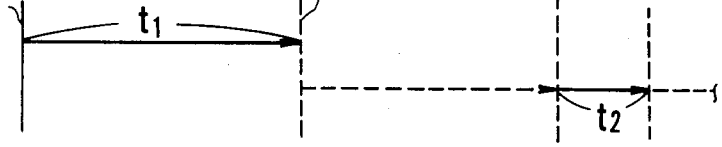

Control of blood pressure measurement exercised by the apparatus of FIG. 1 will now be described with reference to the flowchart of FIG. 2.

When power is introduced at the control unit 7, the power supply is subjected to a battery check and such initial settings as a pressure zeroing adjustment are made at a step S90. At the end of the initial settings, the preparations for blood pressure measurement are completed and the system enters a stand-by mode to await the start of measurement. When blood pressure measurement commences, the program moves to a step S100, which calls for the pressurization setting unit 13 to be set to a pressurization value. This is accomplished by pressing a pressurization switch, which is not shown. When the pressurization switch is pressed, the control unit 7 actuates the pressurization pump 10, which responds by pressurizing the cuff 12 by supplying it with air. Next, at a step S101, the control unit 7 causes the display 8 to display the value of pressure applied to the patient's blood vessel by the pressurized cuff 12. The applied pressure is sensed approximately every 0.5 sec by the pressure sensor 4, the analog output whereof is converted into a digital signal by the A-D converter 6 for application to the control unit 7. Thus, the digital pressure signal is applied to the control unit 7 approximately every 0.5 sec. The control unit 7 compares the pressure signal currently being received with the last pressure signal inputted thereto and renders a decision to the effect that pressurization has taken place when the currently arriving pressure signal indicates a pressure increase of 5 mmHg or more over the last signal. This is to deal with an arrangement in which the pressurization pump 10 is a manually operated pump such as a rubber pressure bulb for performing pressurization by hand.

Next, decision step S102 calls for monitoring to determine whether pressurization has ended. If pressurization ends, the next step executed is a step S103; if not, the program returns to the step S101. Thus, pressure values are displayed in successive fashion. It should be noted that the end of pressurization is indicated when equivalence is established between the value set by the setting unit 13 and the measured value of pressure, or when there is absolutely no increase in pressure over a period of 1 sec.

Step S103 executed at the start of depressurization calls for resetting of the timer circuit 7a in control unit 7, whereby the timer circuit 7a starts measuring time from zero. Next, at a step S104, processing for detecting a Korotkoff sound from the blood flow sound signal produced by the microphone 2 is executed. This step is repeated until the first Korotkoff sound (hereafter referred to as a "K-sound") is detected. When the first K-sound is detected, the program proceeds to a step S105, where a period of time $t_1$ from the start of depressurization to the detection of the first K-sound is stored in an internal memory (not shown) of the control unit 7. This is followed by a step S106, where the value of pressure prevailing at the detection of the first K-sound and sensed by the pressure sensor 14 is displayed by the display 8 as the systolic blood pressure value.

This is followed by a step S107, at which the system waits for detection of the second K-sound. When the second K-sound is detected, the next step S108 calls for a period of time $t_3$ from the start of depressurization to the detection of the second K-sound to be stored in the aforementioned internal memory. Next, at a step S109, the control unit 7 calculates the time interval $t_2$ between the occurrence of the first and second K-sounds by performing the operation $t_2 = t_3 - t_1$, where $t_3$ is the time period found at step S108 and $t_1$ is the time period found at step S105. The control unit 7 then determines at a step S110 whether the inequality $t_1 > t_2$ holds.

In general, measuring systolic and diastolic blood pressure on the basis of K-sounds entails gradually pressurizing the pressure cuff 12 to a pressure greater than the systolic blood pressure, then gradually reducing cuff pressure at a rate of 2–3 mmHg per heartbeat and detecting the occurrence of the sound of blood flowing through the patient's blood vessel while depressurization is being carried out. The value of pressure prevailing at the occurence of the first sound of blood flow is treated as systolic blood pressure. As depressurization proceeds, the sounds of blood flow accompanying such depressurization grow steadily in intensity. At a certain value of pressure, however, the sound of blood flow diminishes and then vanishes. The value of pressure at which the weakening or extinction of the sound is first detected is treated as diastolic blood pressure.

The pressurization-depressurization curve when measuring systolic blood pressure is as shown in FIG. 3. Pressurization begins at point a and is continued until a required value is reached at point b. Depressurization starts at point b, and the initial K-sound, which is the sound of the blood flow, occurs at point c. The value of pressure prevailing at point c is the systolic blood pressure.

Accordingly, if $t_1 > t_2$ is not satisfied (i.e., if $t_1 \leq t_2$ holds) at step S110, then this indicates that the initial pressurization operation was insufficient and there is a high possibility that pressurization was terminated somewhere between the systolic and diastolic blood pressure of the patient. This means that the original detection of systolic blood pressure was erroneous. As a result, the program proceeds from step S110 to a step S111, where the display 8 is made to indicate that pressurization is inadequate and the buzzer 9 is actuated. Next, venting of the air from the cuff 12 proceeds at a step S112. When the value of pressure sensed by the pressure sensor 4 drops below a predetermined value, thus indicating completion of the venting operation, the program returns to the step S100 to re-enable pressure measurement.

If the inequality $t_1 > t_2$ is found to hold at the step S110, the pressure which prevailed at the occurrence of the first K-sound is treated as systolic blood pressure and the program proceeds from step S110 to a step S113. Here the control unit 7 executes processing for measuring diastolic blood pressure, treating as diastolic blood pressure the value of pressure prevailing at the instant the K-sounds weaken or vanish. The control unit 7 causes the display 8 to display the detected value of diastolic pressure at a step S114, thus ending blood pressure measurement.

Thus, in accordance with the present invention as described above, the patient's pulse interval is used to detect inadequate pressurization at the time of blood pressure measurement. This enables inadequate pressurization to be detected in a reliable manner without subjecting the patient to an excessive burden by pressurizing the cuff 12 more than is necessary. In addition, blood pressure is measured reliably since measurement is based on the technically well-established Korotkoff sound pick-up method.

In the illustrated embodiment, elapsed time $t_3$ from the start of depressurization to the occurrence of the second blood flow sound is measured and $t_2$ is found by calculation, as illustrated at (a) in FIG. 4 and described in detail above. However, as shown in FIG. 4(b), the elapsed time $t_2$ from the initial occurrence of the blood flow sound to the second occurence thereof can be measured directly. Further, since it will suffice if $t_2$ is the interval between any two successive pulses of the patient, measurement is not limited to the first two pulses. Accordingly, as shown in FIG. 4(c), measurement can be made a predetermined period of time after the initial blood flow sound to determine the time interval $t_2$ between any two adjacent sounds of blood flow, which at this point in time will exhibit a high degree of stability. Still another possibility is to measure elapsed time covering several of the patient's pulse beats and calculate the pulse-to-pulse interval by taking the average, as shown in FIG. 4(d). Further, as shown in FIG. 4(e), the intervals between a plurality of pulse pairs can be measured and the minimum measured value can be taken as the patient's pulse interval. This will allow inadequate pressurization to be discriminated with greater precision.

Figure 5:
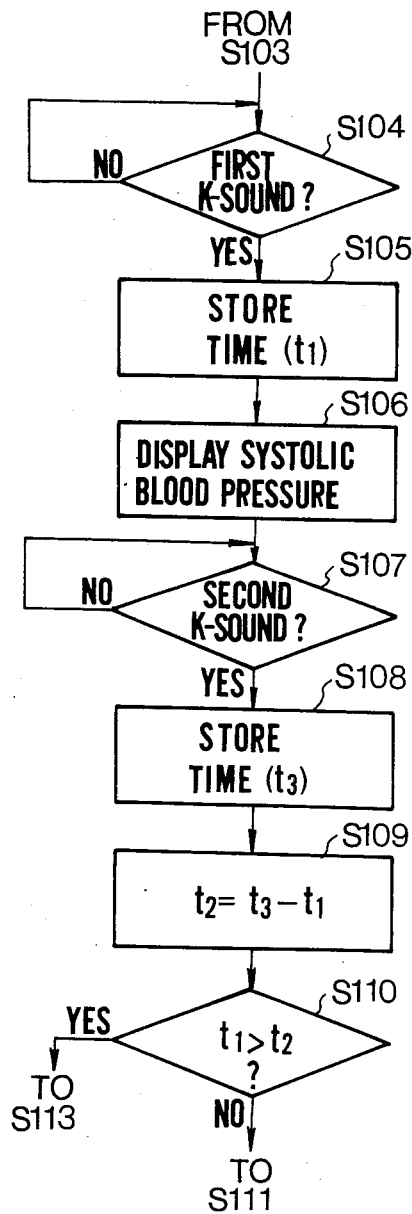
FIGS. 5(a)–5(e) are flowcharts illustrating control of blood pressure measurement according to other embodiments of the present invention.
Figure 5:
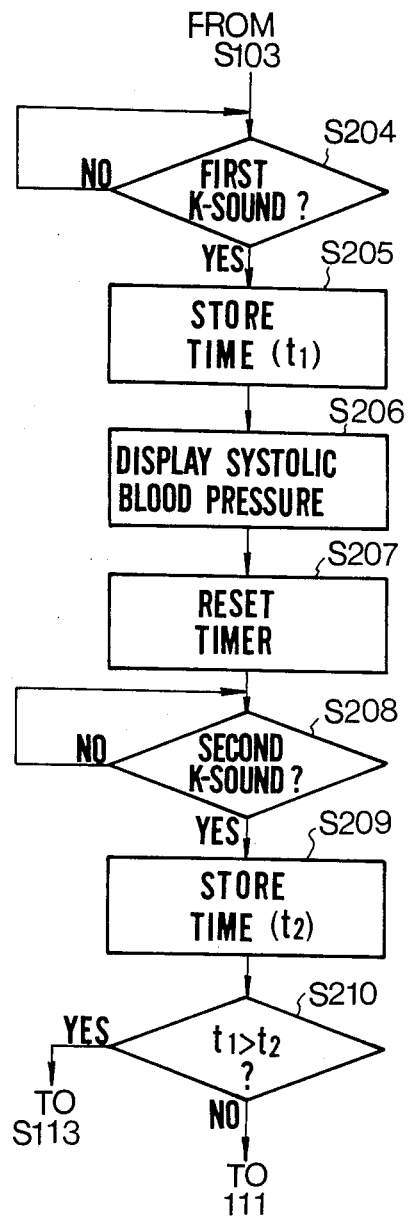
Figure 5:
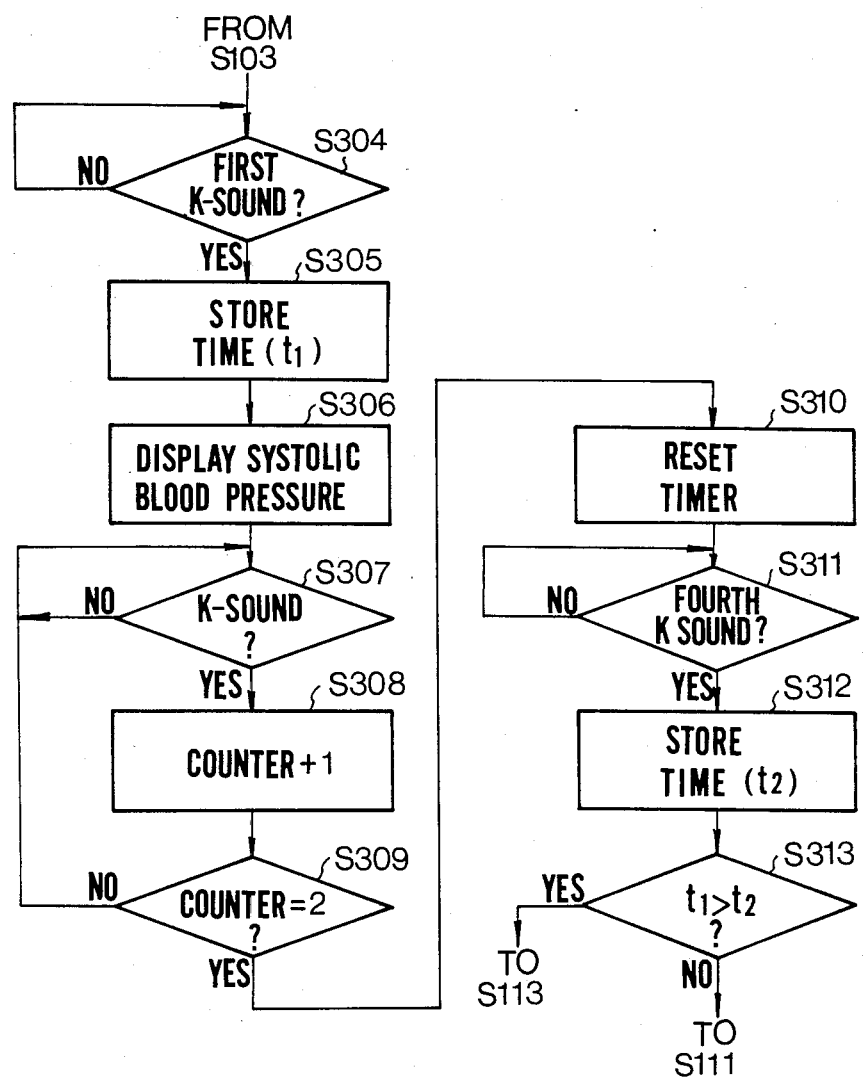
Figure 5:
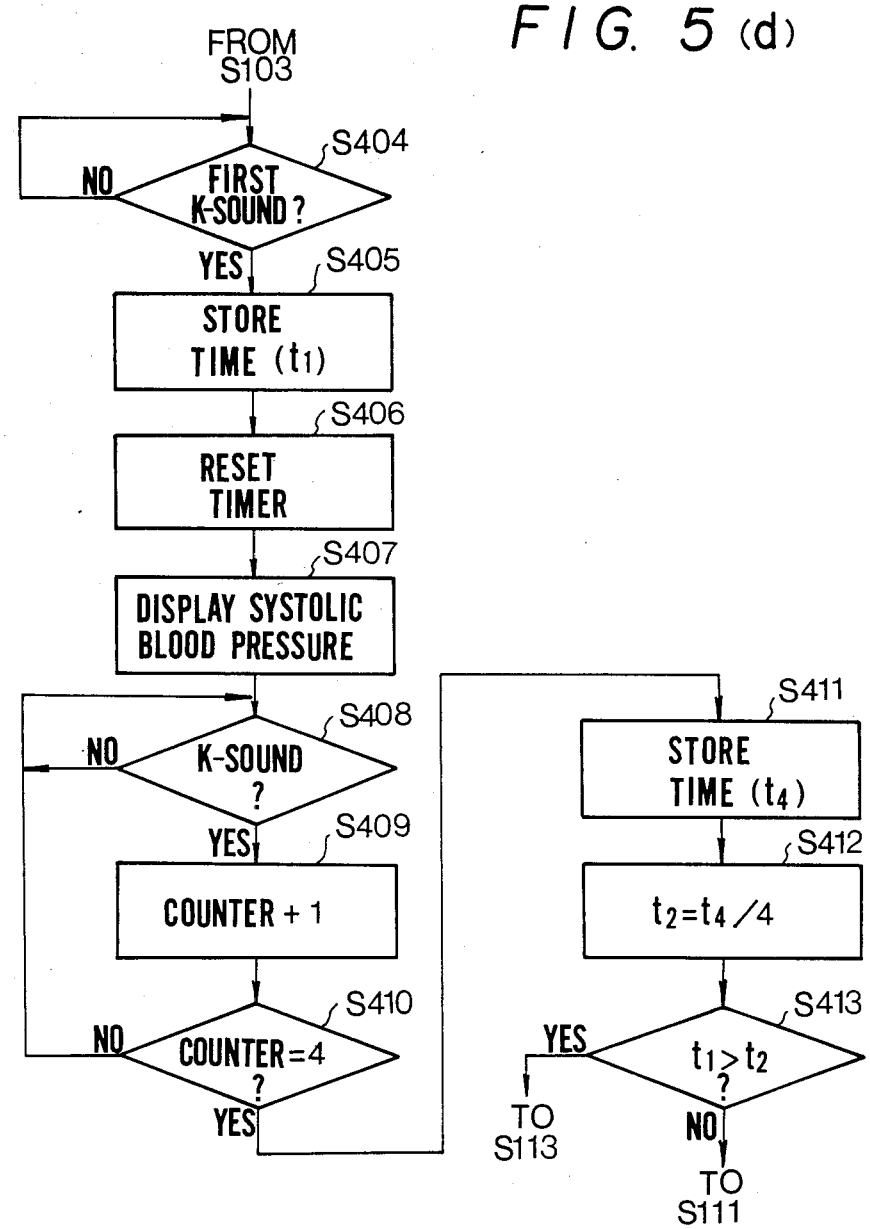

Measurements illustrated by (b) through (e) of FIG. 4 can be achieved by replacing the steps S104 through S110 of the flowchart of FIG. 2, which steps are again shown in FIG. 5(a), by the portions of the flowcharts of FIGS. 5(b) through 5(e). Note that the flowcharts of FIGS. 5(a) through 5(e) correspond to the elapsed time measurements of FIGS. 4(a) through 4(e), respectively.

In FIG. 5(b), the initial K-sound is detected at a step S204 and elapsed time $t_1$ from the start of depressurization is stored in memory at a step S205. The timer 7a is reset at a step S206. Accordingly, after systolic blood pressure is displayed at a step S207, the status of the timer 7a at the instant the second K-sound is detected at a step S208 will indicate the elapsed time $t_2$ from the initial occurrence of the K-sound to the second occurrence thereof.

In FIG. 5(c), steps S304 through S306 call for detecting the initial K-sound, storing the elapsed time $t_1$ from the start of pressurization to the occurrence of the initial K-sound and displaying systolic blood pressure. This is followed by steps S307 through S309, which call for counting a predetermined number (two in this example) of K-sounds, after which the timer 7a is reset at a step S310. When the next K-sound is detected at a step S311, therefore, the status of the timer 7a will indicate the elapsed time $t_2$ from the third to the fourth K-sound.

In FIG. 5(d), steps S404 through S406 call for detecting the initial K-sound, storing the elapsed time $t_1$ from the start of pressurization to the occurrence of the initial K-sound, resetting the timer 7a and displaying systolic blood pressure. Steps S408 through 410 then call for counting a predetermined number (four in this example) of the K-sounds, during which time the timer 4a is measuring elapsed time. The elapsed time $t_4$ in timer 7a is stored in memory at a step S411. Thus $t_4$ indicates elapsed time from the initial K-sound to the fifth K-sound. The elapsed time $t_4$ is divided by four at a step S412 to calculate the average elapsed time $t_2$ between adjacent K-sounds.

In FIG. 5(e), steps S504 through S507 call for detecting the initial K-sound, storing the elapsed time $t_1$ from the start of pressurization to the occurrence of the initial K-sound, resetting the timer 7a and displaying systolic blood pressure. This is followed by steps S508 through S512, which call for detecting the next K-sound and comparing the elapsed time $t_1$ from the start of depressurization to the initial K-sound and elapsed time $t_2$ from the initial K-sound to the second K-sound. The steps S508 through S512 are repeated without a display of inadequate pressurization, even if $t_2$ is greater than $t_1$, until the counter counts up to a predetermined number, i.e., three in this example, at a step S513. Thus, monitoring is continued until the occurrence of the fourth K-sound is detected.

As many apparently widely different embodiments of the present invention can be made without departing from the spirit and scope thereof, it is to be understood that the invention is not limited to the specific embodiments thereof except as defined in the appended claims.

What is claimed is:

1. A blood pressure measuring apparatus in which a pressure cuff is adapted to be affixed to a patient, comprising:
   pressurizing means for feeding a fluid into the pressure cuff to effect pressurization thereof;
   sensing means for sensing blood flow sounds produced by a blood vessel of the patient when the pressure cuff, pressurized by said pressurizing means, is depressurized and for producing an output signal indicative of the blood flow sounds;
   first measuring means for measuring elapsed time from when depressurization starts until said sensing means first generates the output signal indicative of the blood flow sound;
   second measuring means for measuring a pulse interval between blood flow sounds in dependence upon the output signal from said sensing means; and
   decision means for deciding whether pressurization is inadequate on the basis of a relationship between the elapsed time measured by said first measuring means and the pulse interval measured by said second measuring means.

2. The apparatus according to claim 1, wherein the fluid fed into the pressure cuff is air.

3. The apparatus according to claim 1, wherein said sensing means comprises discrimination means for discriminating a Korotkoff sound from other blood flow sound produced by the blood vessel.

4. The apparatus according to claim 1, wherein said decision means comprises:
   comparison means for comparing the elapsed time with the pulse interval to produce a comparison output; and
   output means for producing an inadequate pressurization signal when the comparison output indicates that the elapsed time is shorter than the pulse interval.

5. A blood pressure measuring apparatus in which a pressure cuff is adapted to be affixed to a patient, comprising:
   pressurizing means for feeding a fluid into the pressure cuff to effect pressurization thereof;
   sensing means for sensing a blood flow sound produced by a blood vessel of the patient when the pressure cuff, pressurized by said pressurizing means, is depressurized;
   first measuring means for measuring a first elapsed time from when depressurization starts to occurrence of an initial blood flow sound sensed by said sensing means;
   second measuring means for measuring a second elapsed time from when depressurization starts to occurrence of a second blood flow sound sensed by said sensing means; and
   decision means for deciding whether pressurization is inadequate by determining that the first elapsed time measured by said first measuring means is at least one-half of the second elapsed time measured by said second measuring means.

6. The apparatus according to claim 5, wherein the fluid fed into the pressure cuff is air.

7. The apparatus according to claim 5, wherein said sensing means comprises discrimination means for discriminating a Korotkoff sound from other blood flow sound produced by the blood vessel.

8. The apparatus according to claim 5, wherein said decision means comprises:
   comparison means for comparing the first elapsed time to the second elapsed time to produce a comparison output; and
   output means for producing an inadequate pressurization signal when the comparison output indicates that the first elapsed time is at least one-half of the second elapsed time.

9. A blood pressure measuring apparatus in which a pressure cuff is adapted to be affixed to a patient, comprising:
   pressurizing means for feeding a fluid into the pressure cuff to effect pressurization thereof;
   sensing means for sensing a blood flow sound produced by a blood vessel of the patient when the pressure cuff, pressurized by said pressurizing means, is depressurized;
   first measuring means for measuring a first elapsed time from when depressurization starts to occurrence of an initial blood flow sound sensed by said sensing means;
   second measuring means for measuring a second elapsed time from the occurrence of the initial blood flow sound to occurrence of a second blood flow sound sensed by said sensing means; and
   decision means for deciding whether pressurization is inadequate by determining that the first elapsed time measured by said first measuring means is greater than the second elasped time measured by said second measuring means.

10. The apparatus according to claim 9, wherein the fluid fed into the pressure cuff is air.

11. The apparatus according to claim 9, wherein said sensing means comprises discrimination means for discriminating a Korotkoff sound from other blood flow sound produced by the blood vessel.

12. The apparatus according to claim 9, wherein said decision means comprises:
- comparison means for comparing the first elapsed time to the second elapsed time to produce a comparison output; and
- output means for producing an inadequate pressurization signal when the comparison output indicates that the first elapsed time is shorter than the second elapsed time.

13. A blood pressure measuring apparatus in which a pressure cuff is adapted to be affixed to a patient, comprising:
- pressurizing means for feeding a fluid into the pressure cuff to effect pressurization thereof;
- sensing means for sensing a blood flow sound produced by a blood vessel of the patient when the pressure cuff, pressurized by said pressurizing means, is depressurized;
- first measuring means for measuring a first elapsed time from when depressurization starts to occurrence of an initial blood flow sound sensed by said sensing means;
- second measuring means for measuring, after a predetermined period of time, a second elapsed time within which at least two blood flow sounds are sensed by said sensing means; and
- decision means for deciding whether pressurization is inadequate by determining that the first elapsed time measured by said first measuring means is shorter than the second elapsed time measured by said second measuring means.

14. The apparatus according to claim 13, wherein the fluid fed into the pressure cuff is air.

15. The apparatus according to claim 13, wherein said sensing means comprises discrimination means for discriminating a Korotkoff sound from other blood flow sound produced by the blood vessel.

16. The apparatus according to claim 13, wherein said decision means comprises:
- comparison means for comparing the first elapsed time to the second elapsed time to produce a comparison output; and
- output means for producing an inadequate pressurization signal when the comparison output indicates that the first elapsed time is shorter than the second elapsed time.

* * * * *